(12) United States Patent
Sobek et al.

(10) Patent No.: US 7,378,262 B2
(45) Date of Patent: May 27, 2008

(54) REVERSIBLY MODIFIED THERMOSTABLE ENZYMES FOR DNA SYNTHESIS AND AMPLIFICATION IN VITRO

(75) Inventors: Harald Sobek, Penzberg (DE); Michael Greif, Lenggries (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 351 days.

(21) Appl. No.: 10/317,715

(22) Filed: Dec. 11, 2002

(65) Prior Publication Data

US 2004/0115639 A1    Jun. 17, 2004

(51) Int. Cl.
*C12Q 1/68* (2006.01)
*C12N 9/00* (2006.01)
*C12N 9/22* (2006.01)

(52) U.S. Cl. ............... 435/184; 530/402; 435/199
(58) Field of Classification Search .............. None
See application file for complete search history.

(56) References Cited

U.S. PATENT DOCUMENTS

| | | | |
|---|---|---|---|
| 5,338,671 A | 8/1994 | Scalice et al. | 435/91.2 |
| 5,436,149 A | 7/1995 | Barnes | 435/194 |
| 5,556,772 A * | 9/1996 | Sorge et al. | 435/91.2 |
| 5,773,258 A * | 6/1998 | Birch et al. | 435/91.2 |
| 6,036,923 A | 3/2000 | Laugharn, Jr. et al. | |
| 6,410,277 B1 | 6/2002 | Barnes | 435/91.2 |

FOREIGN PATENT DOCUMENTS

| | | | |
|---|---|---|---|
| DE | EP1088891 | * | 4/2001 |
| EP | 1 088 891 | | 4/2001 |
| EP | 1 130 118 A2 | | 9/2001 |
| GB | EP1078984 | * | 2/2001 |
| US | EP0744470 | * | 11/1996 |
| WO | WO 01/25483 A2 | | 4/2001 |

OTHER PUBLICATIONS

Kellogg DE, et al. "TaqStart Antibody™:"Hot Start" PCR facilitated by a neutralizing monoclonal antibody directed against Taq DNA polymerase", Biotechniques, 1994, vol. 16, No. 6, p. 1134-1137.*

Klenk, H., et al., 1997, "The complete genome sequence of the hyperthermophlic sulphate-reducing archaeon *Archaeoglobus fulgidus*", Nature, 390:361-370.

Klenk, H., et al., 1997, "*Archaeoglobus fulgidus* section 144 of 172 of the complete genome", Embl/GenBank/DDBJ, The Institute of Genomic Research,, XP002130948.

Rudd, Edwin A.; "Reversible Inhibition of Lambda Exonuclease with High Pressure"; 1997, *Biochemical and Biophysical Communications*, vol. 230, pp. 140-142.

* cited by examiner

*Primary Examiner*—Gary Benzion
*Assistant Examiner*—Stephanie K. Mummert
(74) *Attorney, Agent, or Firm*—Rhea C. Nersesian; Townsend and Townsend and Crew, LLP

(57) ABSTRACT

The invention relates to a composition comprising a first modified thermostable enzyme exhibiting 3'exonuclease activity but essentially no DNA polymerase activity and a second modified thermostable enzyme exhibiting DNA polymerase activity, whereas the fidelity of an amplification process is enhanced by the use of the composition in an amplification process in comparison to the use of the single second enzyme in an amplification process and, whereas said first and said second modified thermostable enzyme is reversibly modified by an inhibiting agent which results in essentially complete inactivation of enzyme activity, wherein incubation of said first and said second modified thermostable enzyme in an aqueous buffer at alkaline pH at a temperature less than 25° C. for 20 minutes results in no significant increase in the activity of said first and said second modified thermostable enzyme, wherein incubation at a temperature greater than 50° C. in an aqueous buffer at alkaline pH results in at least tow-fold increase in enzyme activity in less than 20 minutes which allow formation of primer extension products.

11 Claims, 10 Drawing Sheets

REVERSIBLY MODIFIED THERMOSTABLE ENZYMES FOR DNA SYNTHESIS AND AMPLIFICATION IN VITRO

BACKGROUND OF THE INVENTION

1. Field of the Invention

This invention is related to the field of nucleic acid chemistry. Specifically, it is related to methods of amplifying nucleic acid sequences. The invention facilitates the amplification of nucleic acids under conditions of high fidelity. The invention may be used for a variety of industrial, medical and forensical purposes.

2. Description of the Invention

The polymerase chain reaction (PCR) is a well known in vitro method for the amplification of nucleic acid sequences (U.S. Pat. Nos. 4,683,202, 4,684,195, 4,965,188). The reaction uses two sequence specific oligonucleotide primers that hybridize to the opposite strands of the denatured target nucleic acid sequence. A heat-stable DNA polymerase catalyzes the elongation of the primers by incorporating desoxynucleotide monophosphates in the new strand.

The specificity of amplification depends on the specificity of primer hybridization. Under the elevated temperatures used in a typical PCR, the primers hybridize only to the target sequence. Under less stringent conditions, the primers may bind non-specifically to other nucleic acid sequences and initiate the synthesis of unspecific extension products. Amplification of unspecific PCR products can compete with the amplification of the target DNA and can significantly decrease the efficiency of the amplification of the target sequence.

In the past, several methods have been developed to reduce the formation of unspecific PCR products. In one method, referred to as a "hot-start" protocol, at least one critical reagent is withheld from the reaction mixture until the temperature is raised sufficiently to provide the necessary hybridization specificity. In this manner, the reaction mixture does not support the primer extension reaction until the missing component is added.

Hot start methods can be carried out manually by opening the reaction tube after an initial high temperature incubation step and adding the missing reagent. However, manual hot-start methods increase the risk of contamination and are labor intensive. Alternatively, heat labile materials, such as wax, are used to separate reaction components (U.S. Pat. No. 5,411,876). A high temperature pre-reaction incubation melts the heat labile material, thereby allowing the reagents to mix. Another method describes the use of antibodies to inhibit the DNA polymerase activity (U.S. Pat. No. 5,338,671). The antibodies are incubated with the polymerase prior to the set up of the reaction mixture to allow the formation of the antibody-DNA polymerase complex. Antibody inhibition is inactivated by denaturation of the antibody at a high temperature pre-incubation step. Additionally, the formation of extension product can also be inhibited by the addition of reagents like short oligonucleotides aptameres which bind to the DNA polymerase in a heat-reversible manner, thereby inhibiting polymerase activity (Lin & Jayasena (1997) J. Mol. Biol. 271: 100-111). However, the production of antibodies and aptameres is expensive and their application in a polymerase chain reaction may require redesign of the amplification reaction.

Non-specific amplification can also be reduced by the use of a reversibly inactivated thermostable DNA polymerase which can be reactivated by incubation in the amplification reaction mixture at an elevated temperature. Non-specific amplification is reduced because the polymerase is inactive until the temperature of the mixture has been elevated to a temperature which insures specific primer hybridization (U.S. Pat. Nos. 5,773,258; 5,677,152).

Routinely, PCR is performed using the thermostable DNA polymerase from *Thermus aquaticus* (Taq DNA polymerase) which shows a 5'-3' polymerase activity and a 5'-3' polymerase-dependent exonuclease function. However, it does not possess a 3'-5' exonuclease activity (Lawyer et al. (1989) *J. Biol. Chem.* 264: 6427-6437). The 3'-5' exonuclease activity of DNA polymerases is referred to as "proofreading activity". This proofreading activity removes mismatched bases from the 3' end of a primer-template duplex. It may be advantageous as it leads to an increased fidelity of replication during the amplification. As Taq DNA polymerase is deficient in 3'-5' exonuclease activity it does not remove mismatched primer ends. However, it is able to elongate these mismatched primers thereby leading to an incorporation of base errors during amplification. Several thermostable B-type DNA polymerases exhibit 3'-5' exonuclease activity and are used in PCR for the amplification of DNA with high fidelity. E.g., well known in the art are the DNA polymerases derived from *Pyrococcus furiosus* (Pfu DNA polymerase, WO 92/09689), *Pyrococcus woesei* (Pwo DNA polymerase available from Roche Applied Science) and *Thermococcus gorgonarius* (Tgo DNA polymerase, WO 981590).

Thermostable DNA polymerases with proofreading activity are also used in PCR as mixtures of DNA polymerases, at least one polymerase exhibiting such a proofreading activity (U.S. Pat. No. 5,436,149). Recently, a thermostable 3'-5' exonuclease was shown to act as a mismatch correcting enzyme if used in PCR as a mixture with a DNA polymerase (WO 01/23583).

A repetitive series of cycles involving template denaturation, primer annealing, and extension of the annealed primers by the polymerase results in exponential accumulation of a specific DNA fragment. The primer extension products synthesized in a given cycle can serve as a template in the next cycle, therefore the number of target DNA copies approximately doubles every cycle. Thus, even smallest amounts of contaminating DNA from a previous PCR amplifications can be amplified and lead to false positive results (carry-over contamination). Therefore, methods have been developed to avoid such a contamination. In PCR amplifications it is possible to substitute dUTP for dTTP to produce uracil-containing DNA (U-DNA). Treating subsequent PCR reaction mixtures with uracil-DNA glycosylase (UNG) prior to amplification contaminating nucleic acids are degraded and are not suitable for amplification. dUTP can be readily incorporated by pol I-type thermostable DNA polymerases but not by B-type polymerases (Slupphaug et al. (1993) *Anal. Biochem.* 211:164-169). Therefore, B-type DNA polymerases can not be used in PCR amplifications if high fidelity and UNG decontamination is required.

DESCRIPTION OF THE INVENTION

Figure 1:
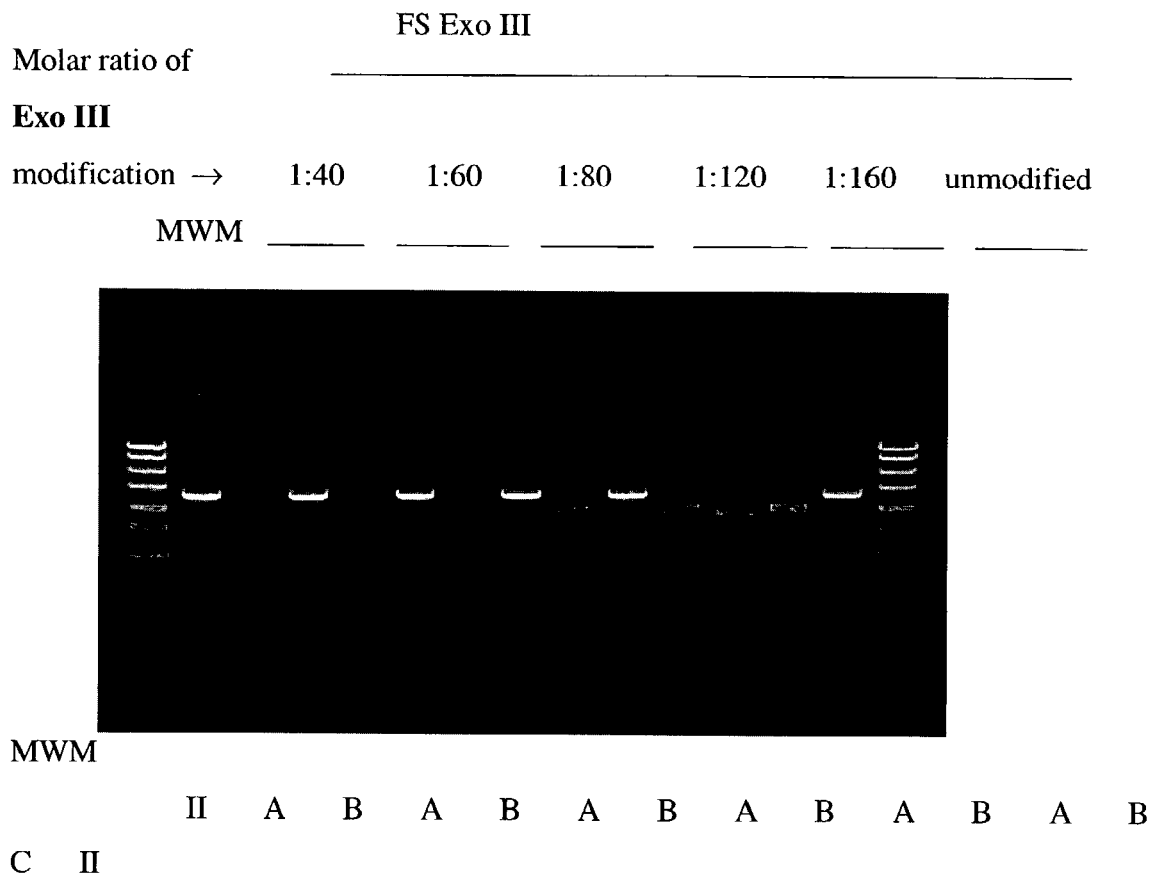
FIG. 1: FS Exo III Activity Assay
Legend:
MWM: Molecular Weight Marker II (Roche Diagnostics GmbH, Cat. No. 236250)
Lane A: samples, stored on ice
Lane B: samples, incubated for 3 h at 80° C.
Lane C: reaction mixture (control)

In the invention described herein, a mixture of thermostable enzymes was developed which is able to perform a hot-start PCR with a high fidelity of replication. The invention provides methods and reagents for the amplification of nucleic acid using a primer-based amplification reaction as specified in the claims. These methods and reagents enable the amplification of nucleic acids with high fidelity of replication and reduced non-specific amplification. Furthermore, the invention enables the application of the UNG decontamination method.

Subject of the present invention is a composition comprising a first modified thermostable enzyme exhibiting 3' exonuclease activity but essentially no DNA polymerase activity and a second modified thermostable enzyme exhibiting DNA polymerase activity, whereas the fidelity of an amplification process is enhanced by the use of the composition in an amplification process in comparison to the use of the single second enzyme in an amplification process and, whereas said first and said second modified thermostable enzyme are reversibly modified by an inhibiting agent which results in essentially complete inactivation of enzyme activity, wherein incubation of said first and said second modified thermostable enzyme in an aqueous buffer at alkaline pH at a temperature less than 25° C. for 20 minutes results in no significant increase in the activity of said first and said second modified thermostable enzyme, wherein incubation at a temperature greater than 50° C. in an aqueous buffer at alkaline pH results in at least two-fold increase in enzyme activity in less than 20 minutes which allow formation of primer extension products.

According to the present invention it is preferred that the first enzyme exhibits 3' exonuclease activity but essentially no DNA polymerase activity and that the second enzyme exhibits DNA polymerase activity but essentially no 3' exonuclease activity. In the examples described below the invention is outlined for the DNA polymerase from *Thermus aquaticus* (Taq DNA polymerase) as the said second thermostable enzyme and the exonuclease III from *Archaeoglobus fulgidus* (Afu Exo III) as the said first thermostable enzyme. As known from the state of the art, suitable enzymes can be derived from other sources, such as thermophilic eubacteria or archaebacteria. Examples are: species of the genera *Thermus, Thermotoga, Thermococcus, Pyrodictium, Pyrococcus*, and *Thermosiphon*. Representative species from which thermostable DNA polymerases useful in PCR amplifications have been derived include *Thermus aquaticus, Thermus thermophilus, Thermotoga maritima, Pyrodictium occultum, Pyrodictium abyssi*, and *Thermosiphon africanus*. Thermostable DNA polymerases are described in U.S. Pat. Nos. 4,889,818; 5,352,600; 5,079,352; PCT/US90/07639; PCT/US91/05753; PCT/US91/0703; PCT/US91/07076; copending U.S. Ser. No. 08/062,368; WO 92/09689, and U.S. Pat. No. 5,210,036; each incorporated herein by references. Thermostable DNA polymerases are available commercially from Perkin Elmer Norwalk, Conn. The methods of the present invention are not limited to the use of the exemplified enzymes.

In a most preferred embodiment of the present invention the first enzyme is a exonuclease exhibiting 3' exonuclease activity and the second enzyme is a Pol I Polymerase exhibiting essentially no 3' exonuclease activity. The use of exonuclease as a first enzyme makes it possible to substitute dUTP for dTTP to produce uracil-containing DNA (U-DNA) in nucleic acid synthesizing reactions as amplification reactions e.g. PCR. Treating subsequent PCR reaction mixtures with uracil-DNA glycosylase (UNG) prior to amplification contaminating nucleic acids are degraded and are not suitable for amplification. Therefore the inventive composition whereas the first enzyme is a exonuclease exhibiting 3'exonuclease activity and the second enzyme is a pol I-type Polymerase exhibiting essentially no 3'exonuclease activity is most preferred because of the possibility of "carry over prevention".

The activities of the enzymes are reversible blocked by a reaction between the enzymes and an inhibiting reagent, which results in the loss of all, or nearly all, of the enzymes activities. The inhibiting reagent is chosen such that the inhibition is reversible at elevated temperatures. In one embodiment the inhibiting agent may be an antibody that is able to inhibit one of said thermostable enzymes. Optionally instead of using an antibody, the enzyme can be inhibited by another inhibiting agent which results in a reversible chemical modification of one of said thermostable enzymes. As described in the present invention, reversible inactivation of thermostable enzymes can be carried out by chemical modification of lysine residues. This chemical modification of lysine can be performed by acid anhydrides (EP 0 962 526). However, chemical modification of other amino acid residues may result in a modified protein with suitable characteristics. A number of compounds have been described in the literature which react with amino groups in a reversible manner. For example, amino groups have been reversibly modified by trifluoroacetylation (see Goldberger and Anfinsen, 1962, Biochemistry 1:410), amidination (see Hunter and Ludwig, 1962, J. Amer. Chem. Soc. 84:3491), malaylation (see Butler et al., 1967, Biochem. J. 103:78) acetoacetylation (se Marzotto et al., 1967, Biochem. Biophys. Res. Commun. 26:517; and Marzotto et al., 1968, Biochim. Biophys. Acta 154:450), tetrafluorosuccinylation (see Brannitzer et al., 1968, Hoppe-Seylers's Z. Physiol. Chem. 349:265), and citraconylation (see Dixon and Perham, 1968, Biochem. J. 109:312-314; and Habeeb and Atassi, 1970, Biochemistry 9 (25):4939-4944.

Preferred reagents for the chemical modification of the epsilon-amino group of lysine residues are dicarboxylic acid anhydrides. Therefore, according to the present invention a composition is preferred whereas said first and said second modified thermostable enzyme is produced by a reaction of a mixture of said first or said second modified thermostable enzyme, respectively, and a modifier reagent, wherein said reaction is carried out at alkaline pH at a temperature which is less than about 25°, wherein said reagent is dicarboxylic anhydride of the general formula:

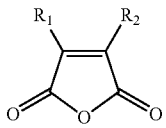

where R1 and R2 are hydrogen or organic radicals, which may be linked, or of the general formula:

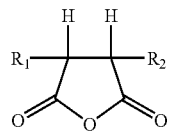

where R1 and R2 are organic radicals, which may be linked, and the hydrogen are cis and wherein said reaction results in essentially complete inactivation of enzyme activity.

The organic radical may be directly attached to the ring by a carbon-carbon bond or through a carbon-hereoatom bond, such as a carbon-oxygen, carbon-nitrogen, or carbon-sulphur bond. The organic radicals may also be linked to each other to form a ring structure as in, for example, 3,4,5,6-tetrahydrophthalic anhydride.

Examples of the preferred reagents include maleic anhydride; substituted maleic anhydrides such as citraconic anhydride, cis-aconitic anhydride, and 2,3-dimethylmaleic anhydride; exo-cis-3,6-endoxo-$\Delta.^4$-tetrahydropthalic anhydride; and 3,4,5,6-tetrahydrophthalic anhydride. The reagents are commercially available from, for example, Aldrich Chemical Co. (Milwaukee, Wis.), Sigma Chemical Co. (St. Louis, Mo.), or Spectrum Chemical Mfg. Corp (Gardena, Calif.). Modifications of thermostable DNA polymerases using the substituted maleic anhydride reagents citraconic anhydride and cis-aconitic anhydride are described in the Examples.

The relative stabilities of the amino groups acylated using the above reagents decreases in the following order: maleic anhydride; exo-cis-3,6-endoxo-$\Delta.^4$-tetrahydroptalic anhydride; citraconic anhydride; 3,4,5,6-tetrahydrophthalic anhydride; cis-aconitic anhydride; and 2,3-dimethylmaleic anhydride (see Palacian et al., supra).

The methods of the present invention are not limited to the exemplified modifier compounds or to the modification of the protein by chemical modification of lysine residues. Any of the compounds described in the literature which react with proteins to cause the reversible loss of all, or nearly all, of the enzyme activity, wherein the modification is reversible by incubation at an elevated temperature in the amplification reaction buffer, is suitable for preparation of a reversibly inactivated enzyme. As new compounds which reversibly modify proteins become available, these too will be suitable for use in the present methods. Thus, compounds for the preparation of the modified thermostable enzymes of the present invention include compounds which satisfy the following properties:

(1) reaction with a thermostable enzyme which catalyzes primer extension results in a significant inactivation of the enzyme;

(2) incubation of the resulting modified enzyme in an aqueous buffer at about pH 8-9 at a temperature at or below about room temperature (25° C.) results in no significant increase in enzyme activity in less than about 20 minutes; and (3) incubation of the resulting modified thermostable enzyme in an amplification reaction buffer, formulated to about pH 8-9 at room temperature, at an elevated temperature greater than about 50° C. results in at least a two-fold increase in enzyme activity in less than about 20 minutes.

Especially preferred according to the present invention is the use of citraconic anhydride or cis-aconitic anhydride as modifier agent, most preferred is cis-aconitic anhydride.

Most preferred are compositions comprising said first and said second modified thermostable enzyme that are reversibly modified with a chemical modification whereas incubation of said first and said second modified thermostable enzyme in an aqueous buffer at alkaline pH at a temperature less than 70° C. for 10 minutes results in no significant increase in the activity of said first and said second modified thermostable enzyme, wherein an incubation at temperatures greater than 70° C. in an aqueous buffer at alkaline pH results in at least two-fold increase in enzyme activity in less than 10 minutes which allow formation of primer extension product. Suitable modifications that lead to such preferred composition are described above.

The terms "nucleic acid" and "oligonucleotide" refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine base. There is no intended distinction in length between the terms "nucleic acid" and "oligonucleotide", and these terms will be used interchangeably. These terms refer only to the primary structure of the molecule. Thus, these terms include double-and single-stranded DNA, as well as double-and single-stranded RNA. Oligonucleotide can be prepared by any suitable method. A review of synthesis methods is provided in Goodchild, 1990, *Bioconjugate Chemistry* 1(3):165-187, incorporated herein by reference.

The term "hybridization" refers the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which only fully complementary nucleic acid strands will hybridize are referred to as "stringent hybridization conditions" or "sequence-specific hybridization conditions". Stable duplexes of substantially complementary sequences can be achieved under less stringent hybridization conditions. Those skilled in the art of nucleic acid technology can determine duplex stability empirically considering a number of variables including, for example, the length and base pair concentration of the oligonucleotides, ionic strength, and incidence of mismatched base pairs, following the guidance provided by the art (see, e.g., Sambrook et al., 1989, supra).

Generally, stringent hybridization conditions are selected to be about 5° C. lower than the thermal melting point (Tm) for the specific sequence at a defined ionic strength and pH. The Tm is the temperature (under defined ionic strength and pH) at which 50% of the base pairs have dissociated. Relaxing the stringency of the hybridization conditions will allow sequence mismatches to be tolerated; the degree of mismatch tolerated can be controlled by suitable adjustment of the hybridization conditions.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. Oligonucleotide analogues, such as "peptide nucleic acids", can act as primers and are encompassed within the meaning of the term "primer" as used herein. A primer is preferably a single-stranded oligodeoxyribonucleotide. The appropriate length of a primer depends on the intended use of the primer but typically ranges from 6 to 50 nucleotides. Short primer molecules generally require cooler temperatures to form sufficiently stable hybrid complexes with the template. A primer need not reflect the exact sequence of the template nucleic acid, but must be sufficiently complementary to hybridize with the template.

The term "primer extension" as used herein refers to both to the synthesis of DNA resulting from the polymerization of individual nucleoside triphosphates using a primer as a point of initiation, and to the joining of additional oligonucleotides to the primer to extend the primer. As used herein, the term "primer extension" is intended to encompass the ligation of two oligonucleotides to form a longer product which can then serve as a target in future amplification cycles. As used herein, the term "primer" is intended to encompass the oligonucleotides used in ligation-mediated amplification processes which are extended by the ligation of a second oligonucleotide which hybridizes at an adjacent position.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning of the amplified product. The region of the primer which is sufficiently complementary to the template to hybridize is referred to herein as the hybridizing region.

The terms "target region" and "target nucleic acid" refers to a region or subsequence of a nucleic acid which is to be amplified. The primer hybridization site can be referred to as the target region for primer hybridization.

As used herein, an oligonucleotide primer is "specific" for a target sequence if the number of mismatches present between the oligonucleotide and the target sequence is less than the number of mismatches present between the oligonucleotide and non-target sequences which may be present in the sample. Hybridization conditions can be chosen under which stable duplexes are formed only if the number of mismatches present is no more than the number of mismatches present between the oligonucleotide and the target sequence. Under such conditions, the oligonucleotide can form a stable duplex only with a target sequence. Thus, the use of target-specific primers under suitably stringent amplification conditions enables the specific amplification of those target sequences which contain the target primer binding sites. The use of sequence-specific amplification conditions enables the specific amplification of those target sequences which contain the exactly complementary primer binding sites.

The term "non-specific amplification" refers to the amplification of nucleic acid sequences other than the target sequence which results from primers hybridizing to sequences other than the target sequence and then serving as a substrate for primer extension. The hybridization of a primer to a non-target sequence is referred to as "non-specific hybridization", and can occur during the lower temperature, reduced stringency pre-reaction conditions.

The term "thermostable enzyme" refers to an enzyme that is relatively stable to heat. The thermostable enzymes can withstand the high temperature incubation used to remove the modifier groups, typically greater than 50° C., without suffering an irreversible loss of activity. Modified thermostable enzymes usable in the methods of the present invention include thermostable DNA polymerases and thermostable exonucleases.

The term "thermostable DNA polymerase" refers to an enzyme that is relatively stable to heat and catalyzes the polymerization of nucleoside triphosphates to form primer extension products that are complementary to one of the nucleic acid strands of the target sequence. The enzyme initiates synthesis at the 3' end of the primer and proceeds in the direction toward the 5' end of the template until synthesis terminates. Purified thermostable DNA polymerases are described in U.S. Pat. Nos. 4,889,818; 5,352,600; 5,079,352; PCT/US90/07639; PCT/US91/05753; PCT/US91/0703; PCT/US91/07076; co-pending U.S. patent application Ser. No. 08/062,368; WO 92/09689; and U.S. Patent No. 5,210,036; each incorporated herein by reference.

The term "thermostable 3'-5'-exonuclease" refers to to an enzyme that is relatively stable to heat and act as a mismatch correcting enzyme if used in PCR as a mixture with a DNA Polymerase. The thermostable 3'-5'-exonuclease removes mismatched nucleic acids from the 3' end of the nascent nucleic acid strand during amplification. Such a thermostable 3'-5'-exonuclease is described e.g. in WO 01/23583.

An enzyme "derived" from an organism herein refers to an enzyme which is purified from the organism or a recombinant version of an enzyme which is purified from the organism, and includes enzymes in which the amino acid sequence has been modified using techniques of molecular biology.

It is preferred that the ratio of said first enzyme to said second enzyme in the inventive composition is in the range of 1:10 to 1:75.

For enzymes derived from other sources and for other methods of chemical modification, different ratios of enzymes may be applied.

Chemical modification of the said enzymes can be performed in buffers at alkaline conditions at a temperture which is less than about 25° C. Buffer components which can be used can include Tris-HCl at a pH of about 7.5 to 9.5. Additional components like KCl, preferably of about 100 mM to 1 M, or detergents, preferably Tween20 of about 0.1% to 2% can be included.

Additional components, however, are not limited to these.

Chemical modification of said first and said second enzyme can be performed by incubation of said enzmes at concentrations of 0.1 mg/ml to 10 mg/ml, preferably at 0.5 mg/ml to 5 mg/ml with the modifier reagent. The modifier reagent can be used in a molar ratio (protein:modifier reagent) of 1:10 to 1:200, preferably 1:10 to 1:100. However, different concentrations and conditions may be applied for different proteins and modifier reagents.

After the chemical modification the protein solution can be dialyzed against storage buffers. Storage buffers can contain Tris-HCl at a pH of about 7.5 to 10, preferably 8.5 to 9.5 and at a concentration of 10 mM to 500 mM, preferably of about 20 mM to 50 mM. Additionally, storage buffers can contain salts, preferably KCl at concentrations of 10 to 500 mM, and other additives like detergents, preferably Tween20, SH-protecting reagents, glycerol and EDTA.

Blends of the said enzymes can be obtained by mixing the enzyme solutions. A further dilution step can also be used to abtain the suitable enzyme blend. In a preferred embodiment of the invention the blends contain polymerase and exonuclease in a range of volume ratios of 10:1 to 75:1. The DNA Polymerase is used in a suitable volume activity, preferably 5 units/µl to 20 units/µl and is mixed with a exonuclease solution that has a suitable concentration (preferably 1 mg/ml to 10 mg/ml). However, different concentrations and ratios can be used to obtain an enzyme blend useful according to the invention.

In a preferred embodiment of the invention said first and said second modified thermostable enzyme accept d-UTP as substrate in chain elongation reactions. According to the present invention it is preferred that said first modified thermostable enzyme is a 3'-5' exonuclease from *Archaeoglobus fulgidus* and whereas said second modified thermostable enzyme is a DNA polymerase from *Thermus aquaticus*.

An embodiment of the present invention is a "reaction mixture" comprising the inventive composition. The term "reaction mixture" refers to a solution containing reagents necessary to carry out a given reaction. An "amplification reaction mixture", which refers to a solution containing reagents necessary to carry out an amplification reaction, typically contains oligonucleotide primers and a DNA polymerase in a suitable buffer. A "PCR reaction mixture" typically contains oligonucleotide primers, a thermostable DNA polymerase, dNTP's, and a divalent metal cation in a suitable buffer. A reaction mixture is referred to as complete if it contains all reagents necessary to enable the reaction, and incomplete if it contains only a subset of the necessary reagents. It will be understood by one of skill in the art that reaction components are routinely stored as separate solutions, each containing a subset of the total components, for reasons of convenience, storage stability, and to allow for independent adjustment of the concentrations of the components depending on the application, and, furthermore, that reaction components are combined prior to the reaction to create a complete reaction mixture.

The methods of the present invention involve carrying out an amplification reaction using heat-activated thermostable enzymes, wherein the active second enzyme or the enzyme composition, respectively, is required for primer extension. Prior to the high temperature incubation which activates the enzyme, the amplification reaction mixture does not support primer extension and no extension products, non-specific or otherwise, are formed. Following the high temperature incubation which reactivates the enzymes, the amplification reaction is maintained at elevated temperatures which insure reaction specificity. Thus, primer extension products are formed only under conditions which insure amplification specificity.

In the methods of the present invention, the heat-activated second enzyme, in its active state, catalyzes the primer extension reaction. For use in a typical amplification reaction, e.g., a PCR, the heat-activated thermostable second enzyme possesses, in its active state, DNA polymerase activity.

A further embodiment of the present invention is a kit for carrying out a polymerase chain reaction comprising the inventive composition.

The present invention also relates to kits, multicontainer units comprising useful components for practicing the present method. A useful kit contains reversibly inactivated thermostable enzymes and one or more reagents for carrying out an amplification reaction, such as oligonucleotide primers, substrate nucleoside triphosphates, cofactors, and an appropriate buffer.

The number of thermocycles can be from about 18 to about 50 cycles depending on the amount of template DNA and its purity.

The inventive method is relatively insensitive to various buffers and various deoxynucleotides and dideoxynucleotide concentrations.

Buffer components which can be used can include Tris-HCl at a pH of about 7.5 to 9.5 and at a concentration of about 50 to 500 mM, preferably of about 100 to 250 mM, $MgCl_2$ at a concentration of about 2 to 6 mM, DMSO at a concentration of about 1 to 5% of the reaction volume, M, Betaine at a concentration of about 0.3 mM, optionally about 0.05 mM 1% mercaptoethanol, about 0.28% Tween20 and/or about 0.02% Nonidet40. Buffer components, however, are not limited to these.

The deacylation of the modified amino groups results from both the increase in temperature and a concomitant decrease in pH. Amplification reactions typically are carried out in a Tris-HCl buffer formulated to a pH of 7.5 to 9.0 at room temperature. At room temperature, the alkaline reaction buffer conditions favor the acylated form of the amino group. Although the pH of the reaction buffer is adjusted to a pH of 7.5 to 9.0 at room temperature, the pH of a Tris-HCl reaction buffer decreases with increasing temperature. Thus, the pH of the reaction buffer is decreased at the elevated temperatures at which the amplification is carried out and, in particular, at which the activating incubation is carried out. The decrease in pH of the reaction buffer favors deacylation of the amino groups.

The change in pH which occurs resulting from the high temperature reaction conditions depends on the buffer used. The temperature dependence of pH various buffers used in biological reactions is reported in Good et al., 1966, Biochemistry 5(2):467-477. For Tris buffers, the change in pKa, i.e., the pH at the midpoint of the buffering range, is related to the temperature as follows: $\Delta.pKa/° C.=-0.031$. For example Tris-HCl buffer assembled at 25° C. undergoes a drop in pKa of 2.17 when raised to 95° C. for the activating incubation.

Although amplification reactions are typically carried out in a Tris-HCl buffer, amplification reactions may be carried out in buffers which exhibit a smaller or greater change of pH with temperature. Depending on the buffer used, a more or less stable modified enzyme may be desirable. For example, using a modifying reagent which results in a less stable modified enzyme allows for recovery of sufficient enzyme activity under smaller changes of buffer pH. An empirical comparison of the relative stabilities of enzymes modified with various reagents, as provided above, guides selection of a modified enzyme suitable for use in particular buffers.

In an especially preferred embodiment of this invention, agents are added to the reaction mixture which lower the melting point of the DNA, such agents can be, for example, glycerine, trehalose and other such agents as betaine or DMSO known to a person skilled in the art.

Deoxynucleotides may be selected from, but not limited to, dGTP, dATP, dTTP and dCTP. However, according to the invention, it is also possible to use derivatives of deoxynucleotides. Deoxynucleotide derivatives are defined as those deoxynucleotides or modified deoxynucleotides which are able to be incorporated by a thermostable DNA polymerase into growing DNA molecules that are synthesized in a thermocycling reaction. Examples of deoxynucleotide derivatives include thionucleotides, 7-deaza-2'-dGTP, 7-deaza-2'-dATP, as well as deoxyinosine triphosphate, that can also be used as a substitute deoxynucleotide for dATP, dGTP, dTTP or dCTP. However, deoxynucleotide derivatives are not limited to these examples. In a preferred embodiment of the invention dUTP is used as a substitute for dTTP to produce uracil-containing DNA (U-DNA) in nucleic acid synthesizing reactions as amplification reactions e.g. PCR.

The aforementioned deoxynucleotides and derivatives thereof are preferably used at a concentration of about 100 μM to about 4 mM.

Another embodiment of the present invention is a method for the amplification of a target nucleic acid contained in a sample comprising the steps of
  contacting said sample with an amplification reaction mixture comprising a primer complementary to said target nucleic acid, deoxynucleotides or derivatives thereof and the inventive composition of said first modified thermostable enzyme and said second modified thermostable enzyme
  incubating the sample and the amplification mixture at a temperature which is greater than about 50° C. for a time sufficient to reactivate said first and said second modified thermostable enzyme and allow for formation of primer extension products.

In a preferred embodiment of the inventive method said first modified thermostable enzyme is a 3'-5' exonuclease from *Archaeoglobus fulgidus* and said second modified thermostable enzyme is a pol I-type DNA polymerase from *Thermus aquaticus*.

In a preferred embodiment of the inventive method one of the deoxynucleotides or derivatives thereof is dUTP and no dTTP is contained in the amplification mixture. The invention composition may be used for amplifying a target nucleic acid. In a preferred embodiment, a PCR amplification is carried out using a reversibly inactivated thermostable DNA polymerase and a reversibly inactivated thermostable enzyme exhibiting 3' exonuclease activity. The annealing temperature used in a PCR amplification typically is about 55-75° C., and the pre-reaction incubation is carried out at a temperature equal to or higher than the annealing temperature, preferably at a temperature greater than about 90° C. The amplification reaction mixture preferably is incubated at about 90-100° C. for up to about 12 minutes to reactivate modified enzymes prior to the temperature cycling.

The first step in a typical PCR amplification consists of heat denaturation of the double-stranded target nucleic acid. The exact conditions required for denaturation of the sample nucleic acid depends on the length and composition of the sample nucleic acid. Typically, an incubation at 90-100° C. for about 10 seconds up to about 4 minutes is effective to fully denature the sample nucleic acid. The initial denaturation step can serve as the pre-reaction incubation to reactivate the DNA polymerase. However, depending on the length and temperature of the initial denaturation step, and on the modifier used to inactivate the enzymes, recovery of the enzymes activity may be incomplete. If maximal recovery of enzyme activity is desired, the pre-reaction incubation may be extended or, alternatively, the number of amplification cycles can be increased.

In a preferred embodiment of the invention, the modified enzyme and initial denaturation conditions are chosen such that only a fraction of the recoverable enzyme activity is recovered during the initial incubation step. Subsequent cycles of a PCR, which each involve a high-temperature denaturation step, result in further recovery of the enzyme activity. Thus, activation of enzyme activity is delayed over the initial cycling of the amplification. This "time release" of DNA polymerase activity has been observed to further decrease non-specific amplification. It is known that an excess of DNA polymerase contributes to non-specific amplification. In the present methods, the amount of DNA polymerase activity present is low during the initial stages of the amplification when the number of target sequences is low, which reduces the amount of non-specific extension products formed. Maximal DNA polymerase activity is present during the later stages of the amplification when the number of target sequences is high, and which enables high amplification yields. If necessary, the number of amplification cycles can be increased to compensate for the lower amount of DNA polymerase activity present in the initial cycles.

An advantage of the methods of the present invention is that the methods require no manipulation of the reaction mixture following the initial preparation of the reaction mixture. Thus, the methods are ideal for use in automated amplification systems and with in-situ amplification methods, wherein the addition of reagents after the initial denaturation step or the use of wax barriers is inconvenient or impractical.

The methods of the present invention are particularly suitable for the reduction of non-specific amplification and for prevention of "carry over" contamination in a PCR. However, the invention is not restricted to any particular amplification system. The reversibly-inactivated enzymes of the present invention can be used in any primer-based amplification system which uses thermostable enzymes and relies on reaction temperature to achieve amplification specificity. The present methods can be applied to isothermal amplification systems which use thermostable enzymes. Only a transient incubation at an elevated temperature is required to recover enzyme activity. After the reaction mixture is subjected to a high temperature incubation in order to recover enzyme activity, the reaction is carried out at an appropriate reaction temperature.

Other amplification methods in addition to the PCR (U.S. Pat. Nos. 4,683,195; 4,683,202; and 4,965,188) include, but are not limited to, the following: Ligase Chain Reaction (LCR, Wu and Wallace, 1989, *Genomics* 4:560-569 and Barany, 1991, *Proc. Natl. Acad. Sci.* USA 88:189-193); Polymerase Ligase Chain Reaction (Barany, 1991, PCR *Methods and Applic.* 1:5-16); Gap-LCR (PCT Patent Publication No. WO 90/01069); Repair Chain Reaction (European Patent Publication No. 439,182 A2), 3SR (Kwoh et al. 1989, *Proc. Natl. Acad. Sci.* USA 86:1173-1177; Guatelli et al. 1990, *Proc. Natl. Acad. Sci.* USA 87:1874-1878; PCT Patent Publication No. WO 92/0880A), and NASBA (U.S. Pat. No. 5,130,238). All of the above references are incorporated herein by reference. This invention is not limited to any particular amplification system. As other systems are developed, those systems may benefit by practice of this invention. A recent survey of amplification systems was published in Abramson and Myers, 1993, *Current Opinion in Biotechnology* 4:41-47, incorporated herein by reference.

Sample preparation methods suitable for each amplification reaction are described in the art (see, for example, Sambrook et al., supra, and the references describing the amplification methods cited above). Simple and rapid methods of preparing samples for the PCR amplification of target sequences are described in Higuchi, 1989, in PCR *Technology* (Erlich ed., Stockton Press, New York), and in *PCR Protocols*, Chapters 18-20 (Innis et al., ed., Academic Press, 1990), both incorporated herein by reference. One of skill in the art will be able to select and empirically optimize a suitable protocol.

Methods for the detection of amplified products have been described extensively in the literature. Standard methods include analysis by gel electrophoresis or by hybridization with oligonucleotide probes. The detection of hybrids formed between probes and amplified nucleic acid can be carried out in variety of formats, including the dot-blot assay format and the reverse dot-blot assay format. (See Saiki et al., 1986, *Nature* 324:163-166; Saiki et al., 1989, *Proc. Natl. Acad. Sci. USA* 86:6230; PCT Patent Publication No. 89/11548; U.S. Pat. Nos. 5,008,182, and 5,176,775; PCR Protocols: A Guide to Methods and Applications (ed. Innis et al., Academic Press, San Diego, Calif.):337-347; each incorporated herein by reference. Reverse dot-blot methods using microwell plates are described in copending U.S. Ser. No. 141,355; U.S. Pat. No. 5,232,829; Loeffelholz et al., 1992, *J. Clin. Microbiol.* 30(11):2847-2851; Mulder et al., 1994, *J. Clin. Microbiol.* 32(2):292-300; and Jackson et al., 1991, *AIDS* 5:1463-1467, each incorporated herein by reference.

Another suitable assay method, referred to as a 5'-nuclease assay, is described in U.S. Pat. No. 5,210,015; and Holland et al., 1991, *Proc. Natl. Acad. Sci.* USA 88:7276-7280; both, incorporated herein by reference. In the 5'-nuclease assay, labeled probes are degraded concomitant with primer extension by the 5' to 3' exonuclease activity of the DNA polymerase, e.g., Taq DNA polymerase. Detection of probe breakdown product indicates both that hybridization between probe and target DNA occurred and that the amplification reaction occurred opending U.S. Ser. Nos. 08/299,682, filed Sep. 1, 1994, and 08/347,657, filed Nov. 23, 1994, both incorporated herein by reference, describe improved methods for detecting the degradation of probe which occurs concomitant with amplification.

An alternative method for detecting the amplification of nucleic acid by monitoring the increase in the total amount of double-stranded DNA in the reaction mixture is described in Higuchi et al., 1992, *Bio/Technology* 10:413-417; Higuchi et al., 1993, *Bio/Technology* 11:1026-1030; and European Patent Publication Nos. 487,218 and 512,334, each incorporated herein by reference. The detection of double-stranded target DNA relies on the increased fluorescence that ethidium bromide (EtBr) and other DNA binding labels exhibit when bound to double-stranded DNA. The increase of double-stranded DNA resulting from the synthesis of target sequences results in a detectable increase in fluorescence. A problem in this method is that the synthesis of non-target sequence, i.e., non-specific amplification, results in an increase in fluorescence which interferes with the measurement of the increase in fluorescence resulting from the synthesis of target sequences. Thus, the methods of the present invention are particularly useful because they reduce non-specific amplification, thereby minimizing the increase in fluorescence resulting from the amplification of non-target sequences.

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

DETAILED DESCRIPTION OF THE PREFERRED EMBODIMENTS

EXAMPLES

Example I

Chemical Modification of Exonuclease III (Exo III)

This example describes the chemical modification of Exo III using cis-aconitic anhydride. Measurements of the activity of the derived Exo III which indicate the molar ratio of modifier to enzyme in the inactivation reaction required to obtain complete inactivation of Exo III activity are described in Example I and Example III.

Recombinant Exo III can be purified from *E. coli* LE 392 (Roche Strain BMTU 7369) as e.g. described in Pat. WO 0123583. Exo III was used at a concentration of 1.3 mg/mL in 50 mM Tris, 300 mM KCl, 1 mM EDTA, 0.2% Tween 20, pH 8.0 at 25° C.

Cis-aconitic anhydride is commercially available (Sigma A-3413, Germany). For one set of modification reactions, the cis-aconitic anhydride was solved in methanol (Merck) in the following concentrations: 26.9 mg/mL, 40.3 mg/mL, 53.8 mg/mL, 80.7 mg/mL, 107.6 mg/mL.

For each solution in the series, 72 μL of solved cis-aconitic anhydride were added to 7.2 mL Exo III solution, resulting in solutions containing molar ratios of Exo III to cis-aconitic anhydride of approximately 1:40, 1:60, 1:80, 1:120 and 1:160. Solutions were incubated over night at 4° C. to inactive the Exo III. After the chemical modification the enzyme was dialyzed against a storage buffer (20 mM Tris, 250 mM KCl, 0.1 mM EDTA, 1 mM DTT, 0.2% Tween 20, 50% glycerol, pH 9.0 at 25° C.). After dialysis the final concentration was 4.9 mg/mL. For the chemically modified enzyme the term FastStart Exo III (FS Exo III) was used.

FS Exo III Activity Assay (agarose gel)

1) Assay

In this assay the degradation of a linear DNA fragment by exonuclease activity was monitored. This example describes activity assay for the FS Exo III both before and after reactivation of FS Exo III by heat incubation. Samples of modified FS Exo III (1:40, 1:60, 1:80, 1:120 and 1:160) and Exo III (unmodified; 4.5 mg/ML) were diluted 1:10 respectively 1:45 in a buffer consisting of 50 mM Tris, 10 mM KCl, 5 mM $(NH_4)_2SO_4$, 2 mM $MgCl_2$. The pH of the buffer was 8.3 at room temperature (FastStart Taq DNA Polymerase PCR buffer; Roche Applied Science (RAS), Cat. No. 2158264). Diluted samples of FS Exo III and Exo III were incubated at 80° C. for 3 hours. Additionally samples were stored on ice as control.

2) Production of the substrate (DNA with 5' extensions)

| | |
|---|---|
| SuRE/Cut Buffer B (10 x conc; RAS, Cat. No. 1417967): | 80 μL |
| pBR 322 DNA (277 ng/μL; RAS, Cat. No. 481238): | 576 μL |
| Bam HI (40 U/μL; RAS, Cat. No. 798975): | 16 μL |
| Water: | 128 μL |

The mix was incubated for 20 minutes at 37° C. and the cleaved DNA was purified with the High Pure PCR Purification Kit (RAS, Cat. No. 1732668). The final concentration of the cleaved DNA (pBR 322×Bam HI) was 141.5 ng/μL.

3) Reaction mixture (15×)

| | |
|---|---|
| Expand High Fidelity PCR buffer (10 x conc.; RAS, Cat. No. 1732641) | 150 μL |
| Substrate (pBR 322 x Bam HI; 141.5 ng/μL) | 105 μL |
| Water | 1095 μL |

To 90 μL of the reaction mixture 10 μL of the enzyme dilution (see above) was added. After incubation for 3 hours at 65° C. the reaction was stopped with 10 μL urea stopper. An aliquot (20 μL) of the reaction was analyzed on a 0.5% agarose gel (FIG. 1).

Under the experimental conditions the chemically modified exonuclease showed no residual activity. After incubation at 80° C. for three hours the exonuclease is reactivated and activity is observed. The degree of residual activity depends on the molar ratio of modifier agent used. The extent of degradation of the linear DNA substrate indicates that for lower ratios of modification a higher activity is observed after reactivation.

Example II

Chemical modification of Taq DNA polymerase:

This example describes the chemical modification of Taq DNA polymerase using cis-aconitic anhydride. Recombinant Taq DNA polymerase (Taq) purified from *E. coli* was used at a concentration of 1.22 mg/mL in 50 mM Tris, 300 mM KCl, 1 mM EDTA, 0.2% Tween 20, pH 8.0 at 25° C.

For the modification reaction, the cis-aconitic anhydride was solved in methanol in a final concentration of 22.0 mg/mL. 1061 μL of cis-aconitic anhydride solution were added to 106.1 mL Taq DNA polymerase solution. The solution was incubated overnight at 4° C. to inactive the Taq. After the chemical modification the enzyme was dialyzed against a storage buffer (20 mM Tris, 100 mM KCl, 0.1 mM EDTA, 1 mM DTT, 0.2% Tween 20, 50% glycerol, pH 9.0 at 25° C.). After dialysis the sample was diluted 1:29 with the storage buffer. For the chemically modified enzyme the term FastStart Taq DNA Polymerase (FS Taq) was used.

The activity of the FS Taq was measured as described in example IV. The enzyme was incubated at 80° C. for three hours to activate the polymerase activity. The enzyme was diluted (1:300-1:700) in storage buffer and the activity was determined as described below. Enzyme samples that were not incubated at 80° C. for three hours showed no activity (<1%).

Example III

Reactivation of the FS Exo III

1) Test principle

To test the exonuclease activity the samples of the enzyme were incubated with 1 μg $^3$H-labled DNA for 1 h at 65° C. and the release of $^3$H-labeled nucleotides was measured.

2) Procedure

Reactivation

FS Exo III (1:40 modification; c=4.9 mg/mL) was diluted 1:10 in FastStart Taq DNA Polymerase PCR buffer (RAS, Cat. No. 2158264). 100 μL aliquots were incubated for 10 min at different temperatures (65° C., 70° C., 75° C., 80° C., 85° C., 90° C.)

Reaction mixture (10×)

| | |
|---|---|
| Expand High Fidelity PCR buffer (10 x conc., RAS, Cat. No. 1732641) | 100 μL |
| $^3$H-DNA (ca. 0.25 μg/μL) | 200 μL |
| Water | 340 μL |

To aliquots of the reaction mixture (64 μl) samples of the preincubated exonuclease (36 μl, corresponding to 18 μg FS Exo III) were added. After incubation for 1 hour at 65 ° C. the samples were chilled on ice. DNA was precipitated by adding 100 μL of hering sperm DNA (1 mg/mL) and 300 μL of 10% TCA solution. After storage on ice for 20 min the samples were centrifuged. Aliquots of the supernatant (400 μL) were removed and counted in a β-counter in 2 mL scintillation fluid (Formula 989, Packard Bioscience B.V.). Calculated Acpm values were used to quantify the reactivation rate of FS Exo III.

Figure 2:
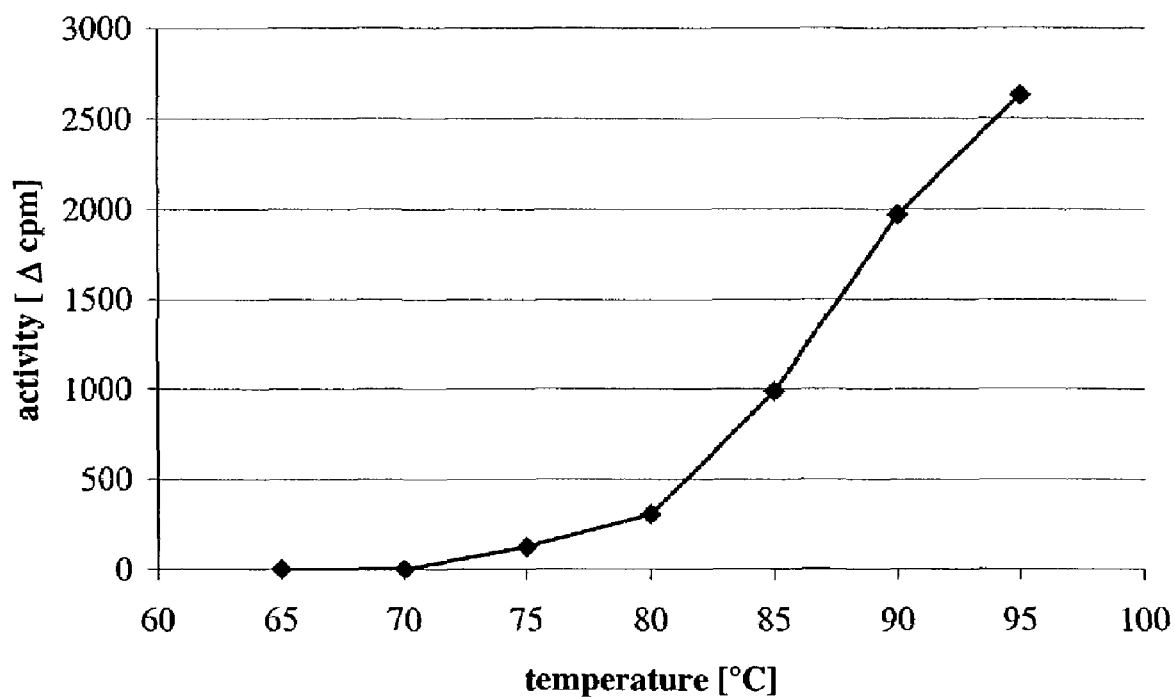
FIG. 2: FS Exo III, temperature dependence of reactivation

Under the experimental conditions reactivation of FS Exo III is observed at incubation temperatures higher than 70° C. At temperatures up to 70° C. no activation is observed (see FIG. 2).

Example IV

Reactivation of the FS Taq

1) Test principle

In this test to assay the activity of FS Taq, unlabelled nucleotides and labelled $\alpha^{32}$ P-dCTP are incorporated by polymerase activity into a synthetic DNA. A template/primer hybrid is used as substrate. The template/primer hybrid consists of M13mp9ss DNA hybridized to a M13 sequencing primer (5'-GTA AAA CGA CGG CCA GT-3'). The synthesized product is precipitated with TCA and the incorporated $\alpha^{32}$P-dCTP is quantified using a scintillation counter.

2) Procedure

Preincubation

FS Taq (5 U/µL, RAS, Cat. No. 2158264) was diluted 1:10 in FastStart Taq-DNA-Polymerase PCR buffer; RAS, Cat. No. 2158264). 50 µL aliquots were incubated for 10 min at different temperatures (65° C., 70° C., 75° C., 80° C., 85° C., 90° C., 95° C.). After preincubation the samples were diluted 1:30 with storage buffer (20 mM Tris, 100 mM KCl, 0.1 mM EDTA, 1 mM DTT, 0.2% Tween 20, 50% glycerol, pH 9.0 at 25° C.).

Test Mix

Reactions were carried out in a 50 µL volume containing the following reagents: 67 mM Tris, pH 8.3 at 25° C., 5 mM MgCl$_2$, 10 mM mercaptoethanol, 0.2% polydocanol, 0.2 mg/mL gelatin, 200 µM dATP, 100 µM dCTP, 200 µM dGTP, 200 µM dTTP, DNA/primer mix (1 µg DNA; 0.3 µg primer) and $\alpha^{32}$ P-dCTP (1 µCi).

3 µL of enzyme dilutions are added to the test mix, mixed well and incubated for 60 min at 65° C. After incubation the samples were placed on ice and the DNA was precipitated with 10% TCA solution. Samples were filtered through GFC-filters (Whatman), the filters were washed three times with 5% TCA, dried and counted in a β-counter in 2 mL scintillation fluid. Calculated Δcpm values were used to quantify the reactivation rate of FS Taq.

Figure 3:
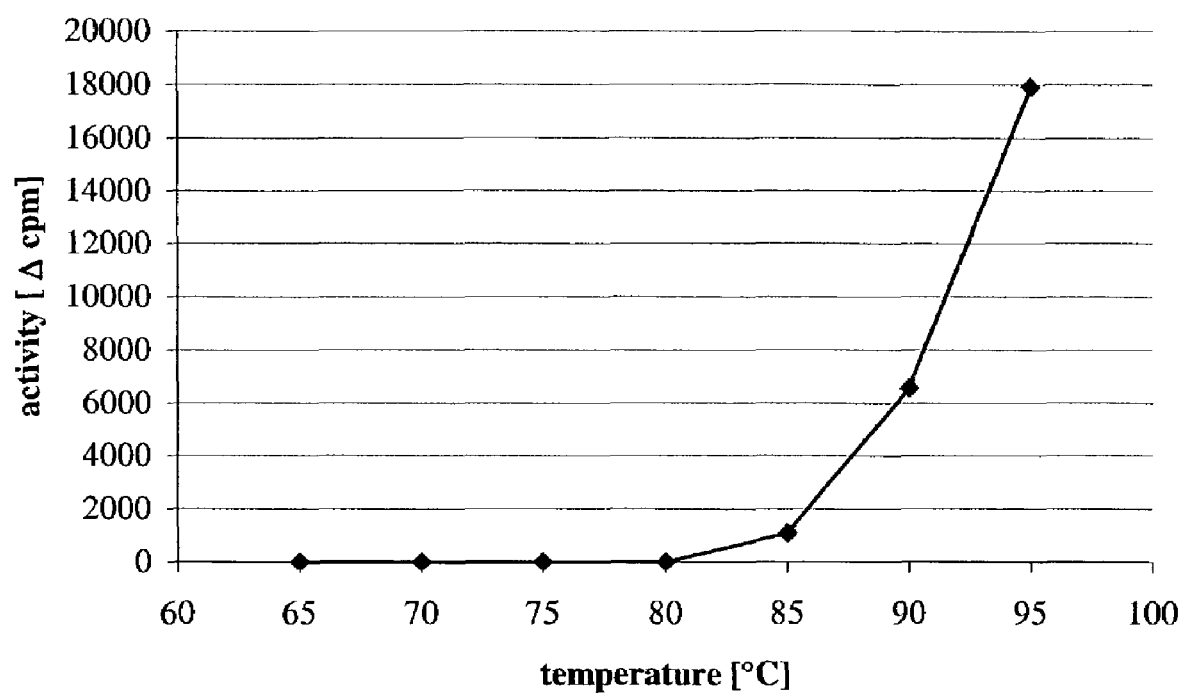
FIG. 3: FS Taq, temperature dependence of reactivation

Under the experimental conditions reactivation of FS Taq is observed at incubation temperatures higher than 80° C. At temperatures up to 80° C. no activation is observed (see FIG. 3).

Example V

Production of Enzyme Blends

1) Taq/Exo III mixture

For amplification reactions Taq/Exo III was used in a ratio of 10:1.

Aliquots (90 µL) of Taq DNA Polymerase (5 U/µL, RAS, Cat. No. 1146173) were mixed with aliquots (10 µL) of Exo III (1 mg/mL) and stored at −20° C.

2) FS Taq/FS Exo III mixture

For amplification reactions FS Taq/FS Exo III was used in ratios of 10:1 and 75:1

For the 10:1 ratio aliquots (90 µL) of FastStart DNA Polymerase (5 U/µL, RAS, Cat. No. 2032929) were mixed with aliquots (10 µL) of Exo III (1:40 modification, 4.9 mg/mL). For the 75:1 ratio 74 µL FastStart Taq DNA Polymerase were mixed with 1 µL FS Exo III. Enzyme blends were stored at −20° C.

Example VI

PCR amplification

1) This example describes the use of the Taq DNA Polymerase, Taq/Exo III mixture (10:1) and FS Taq/FS Exo III mixture (75:1) in PCR amplifications (CF-31).
2) Background information: The CFFR gene is located on the long arm of human chromosome 7. The CF-31 Primer Mix (Linear array CF-31 Kit, RAS, Cat. No. 3017443) contains 28 different primers to simultaneously amplify 14 different regions of this gene.

The PCR was carried out in 100 µL reaction volume under the following reaction conditions.

Reaction Mixtures:

| Taq DNA Polymerase | Taq/Exo III mixture | FS Taq/FS Exo III mixture |
|---|---|---|
| 10 mM Tris, pH 8.3 (20° C.) | 10 mM Tris, pH 8.5 (25° C.) | 50 mM Tris, pH 8.3 (25° C.) |
| 50 mM KCl | 17.5 mM (NH$_4$)$_2$SO$_4$ | 10 mM KCl |
|  | 5 mM (NH$_4$)$_2$SO$_4$ |  |
| 8 mM MgCl$_2$ | 8 mM MgCl$_2$ | 8 mM MgCl$_2$ |
|  | 0.5% Tween 20 (Merck) |  |
|  | 1.5% DMSO (Riedel de Haen) |  |
| 0.12 µM CF-31 Primer Mix | 0.12 µM CF-31 Primer Mix | 0.12 µM CF-31 Primer Mix |
| 0.3 mM dATP, dCTP, dGTP | 0.3 mM dATP, dCTP, dGTP | 0.3 mM dATP, dCTP, dGTP |
| 0.6 mM dUTP | 0.6 mM dUTP | 0.6 mM dUTP |
| 3 unit of UNG (RAS) | 3 unit of UNG (RAS) | 3 unit of UNG (RAS) |
| 3 µL of Taq DNA Polymerase | 3 µL of Taq/Exo III mixture | 3 µL of FS Taq/FS Exo III mixture |
| 100 ng human genomic DNA (RAS) | 100 ng human genomic DNA (RAS) | 100 ng human genomic DNA (RAS) |

Thermal cycling profile:

| | |
|---|---|
| Hold: | 10 min/42° C. |
| Hold: | 2 min/95° C. |
| 32 cycles: | 30 sec/95° C. |
| | 30 sec/60° C. |
| | 60 sec/72° C. |
| Hold: | 10 min/72° C. |
| Hold: | forever 4° C. |

Figure 4:
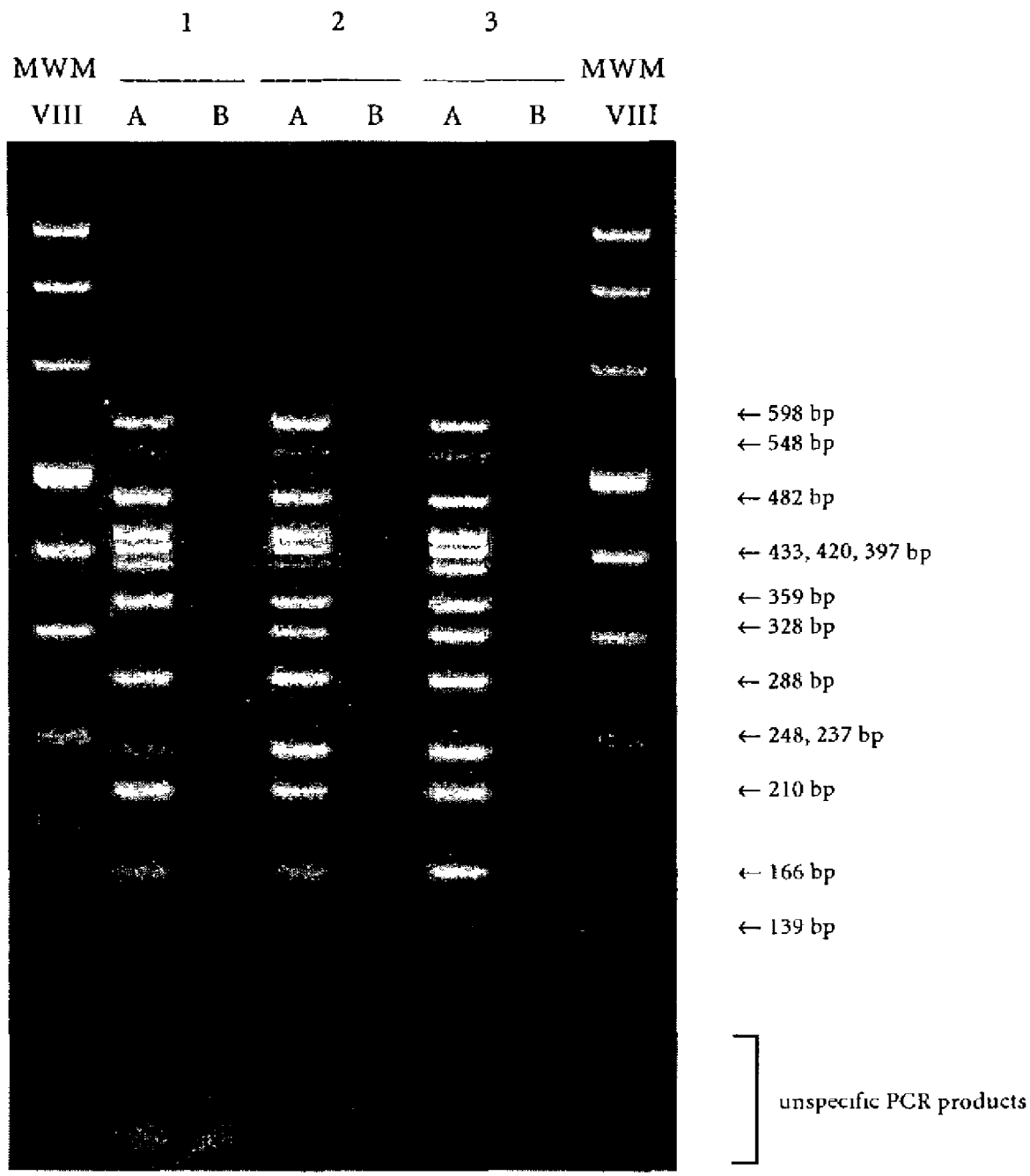
FIG. 4: PCR (CF-31)
Legend:
MWM VIII: Molecular weight marker VIII (Roche Diagnostics GmbH, Cat. No. 1336045)
Lane 1: amplification using Taq DNA polymerase
Lane 2: amplification using Taq/Exo III mixture
Lane 3: amplification using FS Taq/FS Exo mixture
Lanes A: amplification reaction
Lanes B: negative control (amplification without human genomic DNA)

The amplified products were analyzed on a 4% agarose gel (FIG. 4).

Example VII

Mismatched Primer Correction in PCR

1) The repair efficiency of the FS Taq/FS Exo III mixture during PCR was tested with 3' terminally mismatched primers. For PCR amplification primers are used in which the forward primer has one nucleotide at the 3' end which cannot base pair with the template DNA. Excision of the mismatched primer end and amplification of the repaired primer generates a product which can subsequently be cleaved with the restriction endonuclease Bsi EI (New England BioLab), whereas the product arising from the mismatched primer is resistant to cleavage.

The primer sequences used:

```
1. reverse:              5'-GGT TAT CGA AAT CAG CCA CAG CG-3'      (SEQ ID NO: 1)
2. forward (g:t mismatch): 5'-TGG ATA CGT CTG AAC TGG TCA CGG TCT-3' (SEQ ID NO: 2)
```

2) The PCR was carried out in 50 μL reaction volume under following reaction conditions.

Reaction Mixtures:

| FastStart Taq DNA Polymerase | FS Taq/FS Exo III mixture |
|---|---|
| 50 mM Tris, pH 8.3 (25° C.) | 50 mM Tris, pH 8.3 (25° C.) |
| 10 mM KCl | 10 mM KCl |
| 5 mM $(NH_4)_2SO_4$ | 5 mM $(NH_4)_2SO_4$ |
| 2 mM $MgCl_2$ | 2 mM $MgCl_2$ |
| 400 nM reverse Primer | 400 nM reverse Primer |
| 400 nM forward Primer | 400 nM forward Primer |
| 200 μM dNTP-Mix | 200 μM dNTP-Mix |
| 10 ng λ DNA (RAS, Cat. No. 745782) | 10 ng λ DNA (RAS, Cat. No. 745782) |
| 0.5 μL of FastStart Taq DNA Polymerase | 0.5 μL of FS Taq/FS Exo III mixture (10:1) |

Thermal cycling profile:

| Hold: | 5 min/95° C. |
| 40 cycles: | 30 sec/95° C. |
| | 30 sec/64° C. |
| | 60 sec/72° C. |
| Hold: | 4 min/72° C. |
| Hold: | forever 4° C. |

| Expand High Fidelity PCR System | Taq/Exo III mixture |
|---|---|
| 50 mM Tris, pH 8.9 (25° C.) | 10 mM Tris, pH 8.5 (25° C.) |
| 22 mM $(NH_4)_2SO_4$ | 17.5 mM $(NH_4)_2SO_4$ |
| 1.5 mM $MgCl_2$ | 1.25 mM $MgCl_2$ |
| | 0.5% Tween 20 |
| | 1.5% DMSO |
| 400 nM reverse Primer | 400 nM reverse Primer |
| 400 nM forward Primer | 400 nM forward Primer |
| 200 μM dNTP-Mix | 200 μM dNTP-Mix |
| 10 ng λ DNA | 10 ng λ DNA |
| 0.75 μL of Expand HiFi enzymemix | 0.5 μL of Taq/Exo III mixture (10:1) |

Thermal cycling profile:

| Hold: | 2 min/94° C. |
| 40 cycles: | 30 sec/94° C. |
| | 30 sec/60° C. |
| | 60 sec/72° C. |
| Hold: | 4 min/72° C. |
| Hold: | forever 4° C. |

Cleavage with restriction enzyme:

PCR products were subsequently cleaved with the restriction endonuclease Bsi EI.

Figure 5:
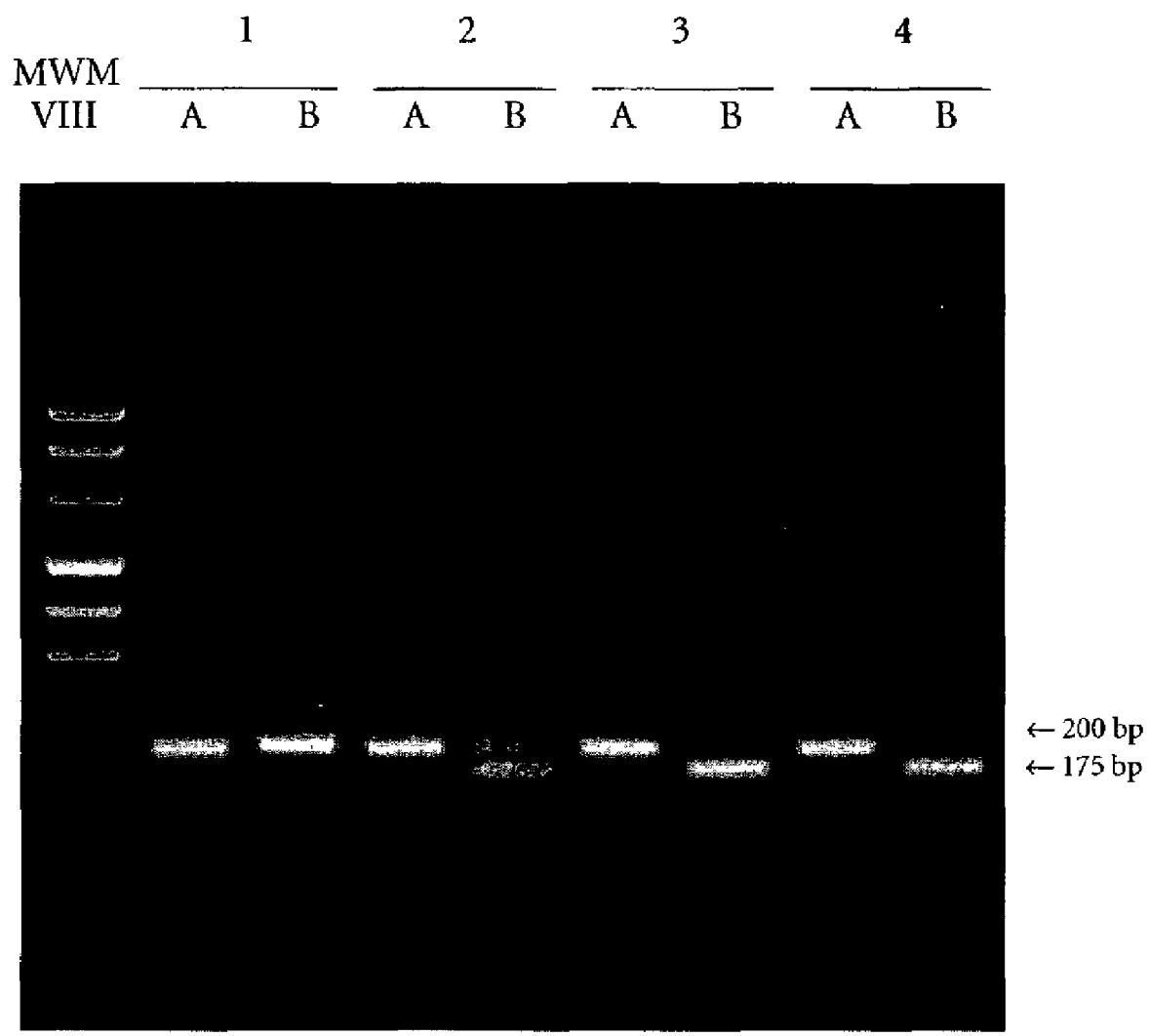
FIG. 5: (Mismatch repair)
Lane 1: amplification using Taq DNA Polymerase
Lane 2: amplification using Expand High Fidelity PCR System
Lane 3: amplification using Taq/Exo III mixture
Lane 4: amplification using FS Taq/FS Exo III mixture
Lanes A: amplification reaction
Lanes B: amplification reaction treated with BsiEI

Five units of the restriction enzyme were added per μg of PCR product. After incubation for 60 min at 60° C. the reaction was stopped and aliquots were analyzed on an agarose gel 8 (see FIG. 5).

Example VIII

UNG Decontamination

1) Uracil DNA glycosylase (UNG, RAS, Cat. No. 1269062) can be used with dUTP to eliminate PCR "carry over" contaminations from previous DNA synthesis reactions. To make PCR products susceptible to degradation, dTTP has to be substituted by dUTP in the PCR reaction mix.

2) The PCR was carried out in 50 μL reaction volume under the following reaction conditions.

Reaction Mixture:

1× FastStart Taq DNA Polymerase PCR buffer (RAS)

200 μM dATP, dCTP, dGTP

600 μM dUTP

```
400 nM tPA Exon 10 primer  (5'-AGA CAG TAC AGC CAG CCT CA-3')  (SEQ ID NO: 3)

400 nM tPA Exon 11 primer  (5'-GAC TTC AAA TTT CTG CTC CTC-3')  (SEQ ID NO: 4)
```

0.5 μL of FS Taq/FS Exo III mixture (75:1)
200 ng Human genomic DNA (RAS)
Thermal cycling profile:

| Hold: | 5 min/95° C. |
|---|---|
| 32 cycles: | 30 sec/95° C. |
| | 30 sec/60° C. |
| | 60 sec/72° C. |
| Hold: | 7 min/72° C. |
| Hold: | forever 4° C. |

Figure 6:
FIG. 6: UNG decontamination
MWM VIII: Molecular weight marker VIII (Roche Diagnostics GmbH)
Lane 1: PCR product without UNG treatment
Lane 2: PCR product treated with UNG

UNG treatment:

Prior to the treatment with uracil-DNA glycosylase (UNG) the PCR products were purified using a commercial purification kit (High Pure PCR Product Purification Kit, RAS, Cat. No. 1732668). Four units of UNG (RAS, Cat. No. 1269062) were used to digest one μg of purified PCR product in a 50 μl reaction volume (1× Taq DNA polymerase PCR buffer). After incubation for one hour at 37° C. 10 μl of 0.6 M NaOH was added. After additional incubation for 5 min at 37° C. 10 μl of 0.6 M HCl were added and aliquots were applied on an agarose gel (see FIG. 6).

Example IX

PCR Amplification (Epo 1,8 kb):

To demonstrate the sensitivity of the FS Taq/FS Exo III mixture a 1,8 kb fragment out of the human Epo gene was amplified using various concentrations of human genomic DNA.

The primer sequences used:

```
Epo 1 forward:
5'-CGC GGA GAT GGG GGT GCA CG-3'   (SEQ ID NO: 5)

Epo 3 reverse:
5'-CAT GCA GCT GCA GGG CTC CCA-3'  (SEQ ID NO: 6)
```

The human genomic DNA dilutions used:
100 ng/μL, 50 ng/μL, 10 ng/μL, 5 ng/μL, 1 ng/μl and 0 ng/μL The PCR was carried out in 50 μL reaction volume under following reaction conditions.

Reaction Mixtures:

| FS Taq/FS Exo III mixture | Taq/Exo III mixture |
|---|---|
| 50 mM Tris, pH 8.3 (25° C.) | 10 mM Tris, pH 8.5 (25° C.) |
| 10 mM KCl | 17.5 mM $(NH_4)_2SO_4$ |
| 5 mM $(NH_4)_2SO_4$ | 1.5 mM $MgCl_2$ |
| 2 mM $MgCl_2$ | 0.5% Tween 20 |
| 5% DMSO (Riedel de Haen) | 1.5% DMSO |
| 400 nM reverse Primer | 400 nM reverse Primer |
| 400 nM forward Primer | 400 nM forward Primer |
| 200 μM dNTP-Mix | 200 μM dNTP-Mix |
| 0.5 μL of FS Taq/FS Exo III mixture (10:1) | 0.5 μL of Taq/Exo III mixture (15:1) |
| 1 μL of different hum. gen. DNA dilutions | 1 μL of different hum. gen. DNA dilutions |

Thermal cycling profile:

| Hold | 5 min/95° C. |
|---|---|
| 35 cycles | 30 sec/95° C. |
| | 2.5 min/72° C. |
| Hold | 4 min/72° C. |
| Hold | forever 4° C. |

Figure 7:
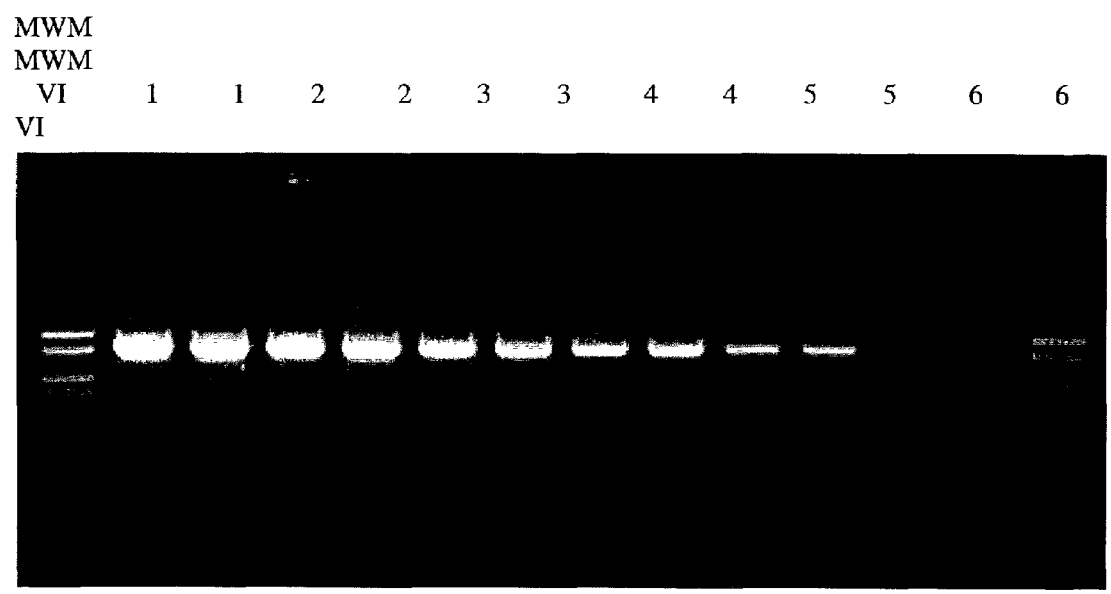
FIG. 7: PCR amplification of Epo, FS Taq/FS Exo III
MWM VI: Molecular weight marker VI (Roche Diagnostics GmbH)
Lane 1: 100 ng human genomic DNA
Lane 2: 50 ng human genomic DNA
Lane 3: 10 ng human genomic DNA
Lane 4: 5 ng human genomic DNA
Lane 5: 1 ng human genomic DNA
Lane 6: 0 ng human genomic DNA
Figure 8:
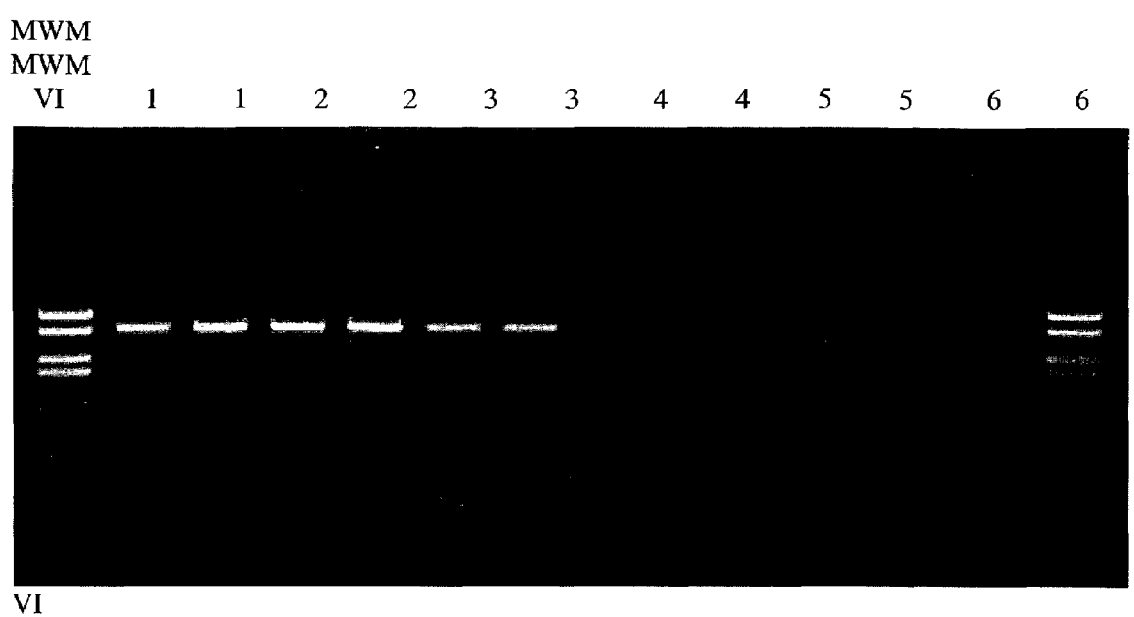
FIG. 8: PCR amplification of Epo, Taq/Exo III
MWM VI: Molecular weight marker VI (Roche Diagnostics GmbH)
Lane 1: 100 ng human genomic DNA
Lane 2: 50 ng human genomic DNA
Lane 3: 10 ng human genomic DNA
Lane 4: 5 ng human genomic DNA
Lane 5: 1 ng human genomic DNA
Lane 6: 0 ng human genomic DNA

The amplified products were analyzed on a 1% agarose gel. The results obtained for FS Taq/FS Exo III mixture are shown in FIG. 7. The results obtained for Taq/Exo III mixture are shown in FIG. 8.

Example X

PCR amplification (tPA 4,8 kb)

To demonstrate the sensitivity of the FS Taq/FS Exo III mixture a 4,8 kb fragment out of the human tPA gene was amplified using various concentrations of human genomic DNA.

The primer sequences used:

```
tPA 7 forward:   5'-GGA AGT ACA GCT CAG AGT TCT GCA GCA CCC CTG C-3'   (SEQ ID NO: 7)

tPA 10 reverse:  5'-GAT GCG AAA CTG AGG CTG GCT GTA CTG TCT C-3'       (SEQ ID NO: 8)
```

The human genomic DNA dilutions used:

100 ng/μL, 50 ng/μL, 10 ng/μL, 5 ng/μL, 1 ng/μl and 0 ng/μL

The PCR was carried out in 50 μL reaction volume under following reaction conditions.

Reaction Mixtures:

| FS Taq/FS Exo III mixture | FastStart Taq-DNA-Polymerase |
|---|---|
| 50 mM Tris, pH 8.3 (25° C.) | 50 mM Tris, pH 8.3 (25° C.) |
| 10 mM KCl | 10 mM KCl |
| 5 mM $(NH_4)_2SO_4$ | 5 mM $(NH_4)_2SO_4$ |
| 1.3 mM $MgCl_2$ | 2 mM $MgCl_2$ |
| 400 nM reverse Primer | 400 nM reverse Primer |
| 400 nM forward Primer | 400 nM forward Primer |
| 200 μM dNTP-Mix | 200 μM dNTP-Mix |
| 0.5 μL of FS Taq/FS Exo III mixture (10:1) | 0.5 μL of FastStart Taq-DNA-Polymerase |
| 1 μL of different hum. gen. DNA dilutions | 1 μL of different hum. gen. DNA dilutions |

Thermal cycling profile:

| | |
|---|---|
| Hold | 5 min/95° C. |
| 10 cycles | 30 sec/95° C. |
| | 4.5 min/68° C. |
| 25 cycles | 30 sec/95° C. |
| | 4.5 min/68° C. |
| | (+20 sec/cycle) |
| Hold | 7 min/68° C. |
| Hold | forever 4° C. |

Figure 9:
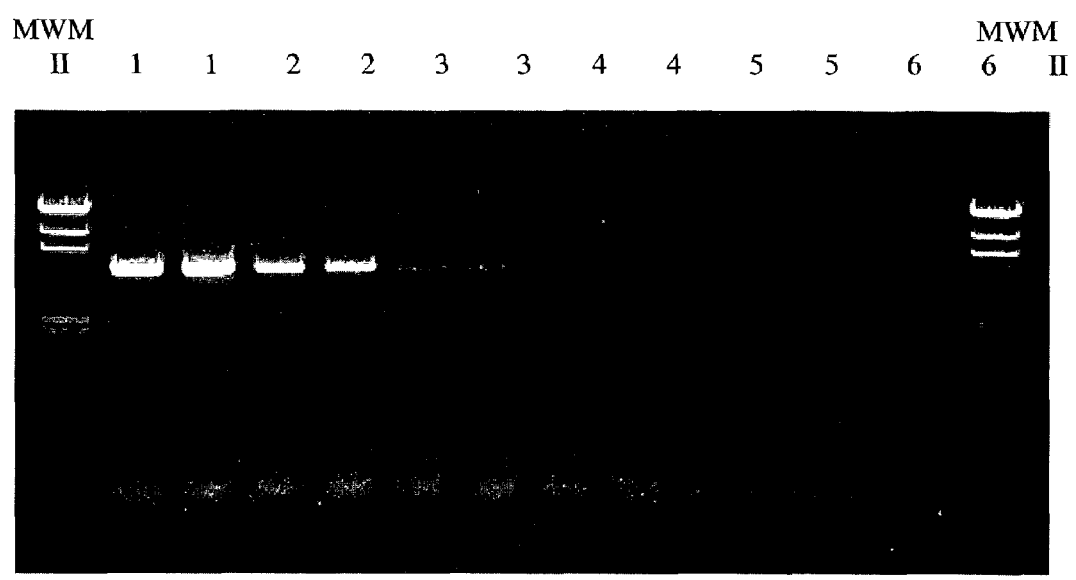
FIG. 9: PCR amplification of tPA,FS Taq/FS Exo III
MWM II: Molecular weight marker II (Roche Diagnostics GmbH)
Lane 1: 100 ng human genomic DNA
Lane 2: 50 ng human genomic DNA
Lane 3: 10 ng human genomic DNA
Lane 4: 5 ng human genomic DNA
Lane 5: 1 ng human genomic DNA
Lane 6: 0 ng human genomic DNA
Figure 10:
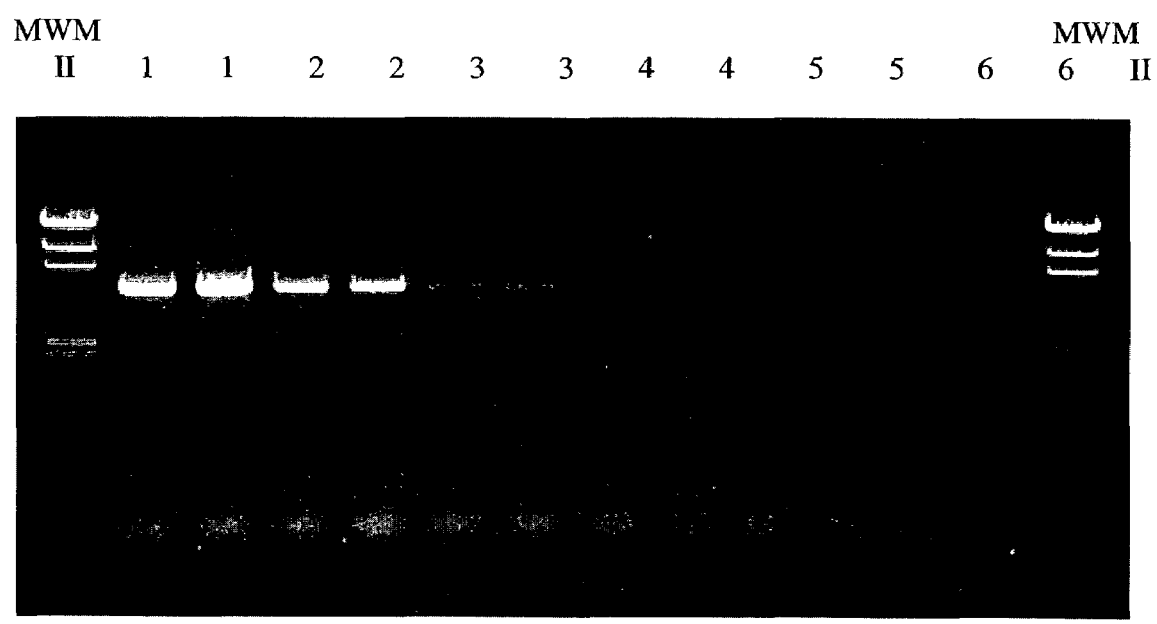
FIG. 10: PCR amplification of tPA, Taq/Exo III
MWM II: Molecular weight marker II (Roche Diagnostics GmbH)
Lane 1: 100 ng human genomic DNA
Lane 2: 50 ng human genomic DNA
Lane 3: 10 ng human genomic DNA
Lane 4: 5 ng human genomic DNA
Lane 5: 1 ng human genomic DNA
Lane 6: 0 ng human genomic DNA

The amplified products were analyzed on a 0.5% agarose gel. The results obtained for FS Taq/FS Exo III mixture are shown in FIG. 9. The results obtained for FastStart Taq-DNA Polymerase are shown in FIG. 10.

---

What is claimed is:

1. Composition comprising a first modified thermostable enzyme exhibiting 3'exonuclease activity but essentially no DNA polymerase activity and a second modified thermostable enzyme exhibiting DNA polymerase activity, whereas the fidelity of an amplification process is enhanced by the use of the composition in an amplification process in comparison to the use of the single second enzyme in an amplification process and, whereas said first and said second modified thermostable enzyme is reversibly modified by an inhibiting agent which results in essentially complete inactivation of enzyme activity, wherein incubation of said first and said second modified thermostable enzyme in an aqueous buffer at alkaline pH at a temperature less than 25° C. for 20 minutes results in no significant increase in the activity of said first and said second modified thermostable enzyme, wherein incubation at a temperature greater than 50° C. in an aqueous buffer at alkaline pH results in at least two-fold increase in enzyme activity in less than 20 minutes which allow formation of primer extension products.

2. Composition according to claim 1 whereas said first and said second modified thermostable enzyme is produced by a reaction of a mixture of said first or said second modified thermostable enzyme, respectively, and a modifier reagent, wherein said reaction is carried out at alkaline pH at a temperature which is less than about 25°, wherein said reagent is dicarboxylic anhydride of the general formula:

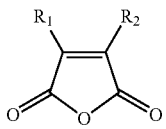

where R1 and R2 are hydrogen or organic radicals, which may be linked, or of the general formula:

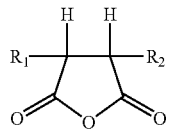

where R1 and R2 are organic radicals, which may be linked, and the hydrogen are cis and wherein said reaction results in essentially complete inactivation of enzyme activity.

3. Composition according to claim 2 whereas said modifier reagent is citraconic anhydride or cis-aconitic anhydride.

4. Composition according to claim 2 whereas said modifier reagent is cis-aconitic anhydride.

5. Composition according to claim 3 whereas incubation of said first and said second modified thermostable enzyme in an aqueous buffer at alkaline pH at a temperature less than 70° C. for 10 minutes results in no significant increase in the activity of said first and said second modified thermostable enzyme, wherein an incubation at temperatures greater than 70° C. in an aqueous buffer at alkaline pH results in at least two-fold increase in enzyme activity in less than 10 minutes which allow formation of primer extension product.

6. Composition according to claim 1 whereas said first and said second modified thermostable enzyme accept d-UTP as substrate in chain elongation reactions.

7. Composition according to claim 1 whereas said first modified thermostable enzyme is a 3'-5' exonuclease from *Archaeoglobus fulgidus* and whereas said second modified thermostable enzyme is a DNA polymerase from *Thermus aquaticus*.

8. A kit for carrying out a polymerase chain reaction comprising a composition according to claim 1.

9. A method for the amplification of a target nucleic acid contained in a sample comprising the steps of
    contacting said sample with an amplification reaction mixture comprising a primer complementary to said target nucleic acid, deoxynucleotides or derivatives thereof and a composition according to claim 1,
    incubating the sample and the amplification mixture at a temperature which is greater than about 50° C. for a time sufficient to reactivate said first and said second modified thermostable enzyme and allow formation of primer extension products.

10. A method according to claim 9 wherein one of the deoxynucleotides or derivatives thereof is d-UTP and wherein no d-TTP is contained in the amplification mixture.

11. Composition according to claim 1, wherein said first and said second modified thermostable enzyme are reversibly modified by an inhibiting agent which results in a reversible chemical modification of said enzymes.

* * * * *

SEQUENCE LISTING

```
<160> NUMBER OF SEQ ID NOS: 8

<210> SEQ ID NO 1
<211> LENGTH: 23
<212> TYPE: DNA
<213> ORGANISM: Artificial Sequence
<220> FEATURE:
<223> OTHER INFORMATION: Reverse PCR primer for mismatch repair test

<400> SEQUENCE: 1
ggttatcgaa atcagccaca gcg                                             23

<210> SEQ ID NO 2
<211> LENGTH: 27
<212> TYPE: DNA
<213> ORGANISM: Artificial Sequence
<220> FEATURE:
<223> OTHER INFORMATION: Forward PCR primer for mismatch repair test

<400> SEQUENCE: 2
tggatacgtc tgaactggtc acggtct                                         27

<210> SEQ ID NO 3
<211> LENGTH: 20
<212> TYPE: DNA
<213> ORGANISM: Artificial Sequence
<220> FEATURE:
<223> OTHER INFORMATION: tPA exon 10 primer for UNG decontamination test

<400> SEQUENCE: 3
agacagtaca gccagcctca                                                 20
```

-continued

```
<210> SEQ ID NO 4
<211> LENGTH: 21
<212> TYPE: DNA
<213> ORGANISM: Artificial Sequence
<220> FEATURE:
<223> OTHER INFORMATION: tPA exon 11 primer for UNG decontamination test

<400> SEQUENCE: 4
gacttcaaat tctgctcct c                                                    21

<210> SEQ ID NO 5
<211> LENGTH: 20
<212> TYPE: DNA
<213> ORGANISM: Artificial Sequence
<220> FEATURE:
<223> OTHER INFORMATION: Human EPO gene forward primer

<400> SEQUENCE: 5
cgcggagatg ggggtgcacg                                                     20

<210> SEQ ID NO 6
<211> LENGTH: 21
<212> TYPE: DNA
<213> ORGANISM: Artificial Sequence
<220> FEATURE:
<223> OTHER INFORMATION: Human EPO gene reverse primer

<400> SEQUENCE: 6
catgcagctg cagggctccc a                                                   21

<210> SEQ ID NO 7
<211> LENGTH: 34
<212> TYPE: DNA
<213> ORGANISM: Artificial Sequence
<220> FEATURE:
<223> OTHER INFORMATION: Human tPA gene forward primer

<400> SEQUENCE: 7
ggaagtacag ctcagagttc tgcagcaccc ctgc                                     34

<210> SEQ ID NO 8
<211> LENGTH: 31
<212> TYPE: DNA
<213> ORGANISM: Artificial Sequence
<220> FEATURE:
<223> OTHER INFORMATION: Human tPA gene reverse primer

<400> SEQUENCE: 8
gatgcgaaac tgaggctggc tgtactgtct c                                        31
```